United States Patent [19]

Bourrain et al.

[11] Patent Number: 5,684,006
[45] Date of Patent: Nov. 4, 1997

[54] ISOXAZOLE AND PYRAZOLE DERIVATIVES AS DOPAMINE RECEPTOR SUBTYPE LIGANDS

[75] Inventors: Sylvie Bourrain, Harlow; Joseph George Neduvelil, Barnet, both of United Kingdom; Paul David Leeson, Monmouth Junction, N.J.; Graham Andrew Showell, Welwyn Garden, United Kingdom

[73] Assignee: Merck, Sharp & Dohme, Ltd., Hoddesdon, England

[21] Appl. No.: 648,083
[22] PCT Filed: Nov. 21, 1994
[86] PCT No.: PCT/GB94/02558
§ 371 Date: May 14, 1996
§ 102(e) Date: May 14, 1996
[87] PCT Pub. No.: WO95/14672
PCT Pub. Date: Jun. 1, 1995

[30] Foreign Application Priority Data

Nov. 25, 1993 [GB] United Kingdom .................. 9324244

[51] Int. Cl.$^6$ .................. A61K 31/495; C07D 401/06
[52] U.S. Cl. .................. 514/252; 514/253; 544/362; 544/364; 544/367; 544/371
[58] Field of Search .................. 514/252, 253; 544/362, 364, 367, 371

[56] References Cited

U.S. PATENT DOCUMENTS

| | | | |
|---|---|---|---|
| 5,318,970 | 6/1994 | Suzuki et al. | 514/252 |
| 5,338,857 | 8/1994 | Ohto et al. | 548/248 |
| 5,342,851 | 8/1994 | Sanfilippo et al. | 514/370 |

FOREIGN PATENT DOCUMENTS

| | | |
|---|---|---|
| 0 289 070 | 4/1988 | European Pat. Off. |
| 0 417 653 A1 | 9/1990 | European Pat. Off. |
| WO 94/21630 | 9/1994 | WIPO |

OTHER PUBLICATIONS

Van Tol, et al. "Cloning of the Gene for a Human Dopamine D4 receptor with High Affinity for the Antipsychotic Clozapine" Nature vol. 350, Apr. 18, 1991 pp. 610–614.

Hawley's Condensed Chemical Dictionary, 11th Edition, 1987.

*Primary Examiner*—Joseph McKane
*Assistant Examiner*—Richard S. Myers, Jr.
*Attorney, Agent, or Firm*—Robert J. North; Melvin Winokur

[57] ABSTRACT

A class of substituted isoxazole and pyrazole derivatives of formula (I), or a salt thereof of or a prodrug thereof, wherein the broken circle represents two non-adjacent double bonds whereby the five-membered ring containing X and Y is aromatic; one of X and Y represents nitrogen, and the other of X and Y represents oxygen or N—$R^5$; $R^1$ represents hydrogen, $C_{1-6}$ alkyl or trifluoromethyl; $R^2$ and $R^3$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^a$, —$NR^aCO_2R^b$, —$COR^a$, —$CO_2R^a$ or —$CONR^aR^b$, $R^4$ represents hydrocarbon or a heterocyclic group; $R^5$ represents hydrogen or $C_{1-6}$ alkyl; and $R^a$ and $R^b$ independently represent hydrogen, hydrocarbon or a heterocyclic group, are ligands for dopamine receptor subtypes within the body and are therefore useful in the treatment and/or prevention of disorders of the dopamine system, in particular schizophrenia.

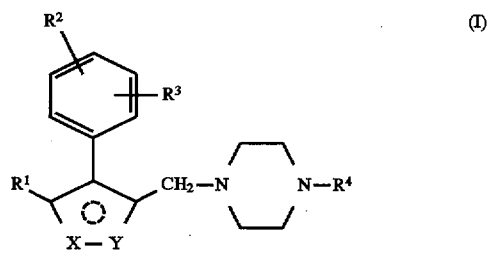

19 Claims, No Drawings

ISOXAZOLE AND PYRAZOLE DERIVATIVES AS DOPAMINE RECEPTOR SUBTYPE LIGANDS

This application is a filing under 35 USC 371 of PCT/GB94/02558, filed Nov. 21, 1994.

This invention relates to a particular class of substituted isoxazole and pyrazole derivatives which are ligands for dopamine receptor subtypes within the body and are therefore of use in the treatment and/or prevention of disorders of the dopamine system, including schizophrenia, depression, nausea, Parkinson's disease, tardive dyskinesias and extrapyramidal side-effects associated with treatment by conventional neuroleptic agents, neuroleptic malignant syndrome, and disorders of hypothalamic-pituitary function such as hyperprolactinaemia and amenorrhoea.

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., Nature (London), 1991, 350, 610) and $D_5$ (Sunahara et al., Nature (London), 1991, 350, 614) receptor subtypes have been described.

The compounds in accordance with the present invention, being ligands for dopamine receptor subtypes within the body, are accordingly of use in the treatment and/or prevention of disorders of the dopamine system.

The present invention accordingly provides a compound of formula I, or a salt thereof or a prodrug thereof:

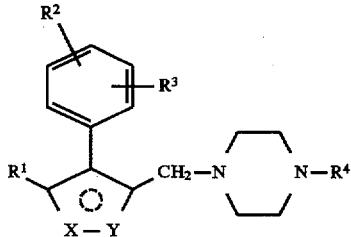

(I)

wherein the broken circle represents two non-adjacent double bonds whereby the five-membered ring containing X and Y is aromatic;

one of X and Y represents nitrogen, and the other of X and Y represents oxygen or N–$R^5$;

$R^1$ represents hydrogen, $C_{1-6}$ alkyl or trifluoromethyl;

$R^2$ and $R^3$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR_b$;

$R^4$ represents hydrocarbon or a heterocyclic group;

$R^5$ represents hydrogen or $C_{1-6}$ alkyl; and $R^a$ and $R^b$ independently represent hydrogen, hydrocarbon or a heterocyclic group.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups include phenyl and naphthyl.

Particular aryl($C_{1-6}$)alkyl groups include benzyl, naphthylmethyl, phenethyl and phenylpropyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, indolyl, aza-indolyl, imidazolyl, oxadiazolyl and thiadiazolyl groups.

Particular heteroaryl($C_{1-6}$)alkyl groups include pyridylmethyl, pyrazinylmethyl, indolylmethyl and aza-indolylmethyl.

The hydrocarbon and heterocyclic groups may in turn be optionally substituted by one or more groups selected from $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$) alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$alkylsulphonyl, arylsulphonyl, trifluoromethane-sulphonyloxy, —NR'R", —NR'COR", —NR'$CO_2$R", —NR'$SO_2$R", —$CH_2$NR'$SO_2$R", —NHCONR'R", —PO(OR') (OR"), —CONR'R", —$SO_2$NR'R" and —$CH_2SO_2$NR'R", in which R' and R" independently represent hydrogen, $C_{1-6}$ alkyl, aryl or aryl ($C_{1-6}$)alkyl.

The term "halogen" as used herein includes fluorine, chlorine, bromine and iodine, especially chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

As will be appreciated, the five-membered heteroaromatic ring containing the moieties X and Y in formula I above is a substituted isoxazole or pyrazole ring.

Suitable values for the substituent $R^1$ include hydrogen, methyl and ethyl, especially methyl.

Suitable values for the substituents $R^2$ and $R^3$ include hydrogen, halogen, cyano, trifluoromethyl, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, methyl, ethyl, isopropyl, nitro, methoxy and chloro. Suitably, at least one of $R^2$ and $R^3$ is hydrogen.

Suitable values for the substituent $R^4$ include aryl($C_{1-6}$) alkyl and heteroaryl($C_{1-6}$)alkyl, any of which groups may be optionally substituted. Examples of suitable substituents on the group $R^4$ include $C_{1-6}$ alkyl, halogen, $C_{1-6}$ alkoxy and nitro.

Particular values of $R^4$ include benzyl, methyl-benzyl, chlorobenzyl, dichlorobenzyl, methoxy-benzyl, nitrobenzyl, naphthylmethyl, phenethyl, phenylpropyl, pyridylmethyl and aza-indolylmethyl.

Suitably, $R^5$ is hydrogen or methyl.

A particular sub-class of compounds according to the invention is represented by the compounds of formula IIA, and salts and prodrugs thereof:

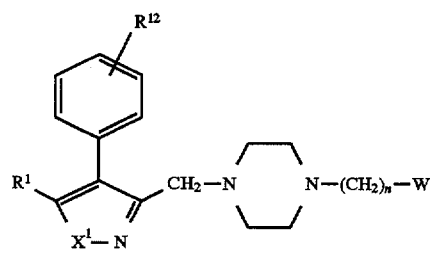

wherein $R^1$ is as defined with reference to formula I above;

$X^1$ represents oxygen or N—$R^5$ in which $R^5$ is as defined with reference to formula I above;

$R^{12}$ represents hydrogen, halogen, cyano, trifluoromethyl, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl;

n is 1, 2, 3 or 4, preferably 1; and

W represents a group of formula (i) or (ii):

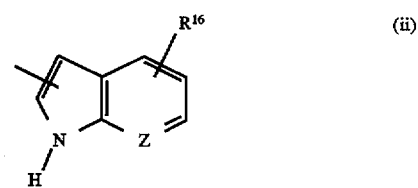

in which

Z represents nitrogen or CH; and $R^{16}$ represents hydrogen, halogen, nitro, $C_{1-6}$ alkyl or $C_{1-6}$ alkoxy.

Particular values of $R^{12}$ with reference to formula IIA above include hydrogen, methyl, ethyl, isopropyl, nitro, methoxy and chloro.

Suitably, $X^1$ is oxygen, NH or N-methyl.

Particular values of $R^{16}$ include hydrogen, chloro, nitro, methyl and methoxy, Another sub-class of compounds according to the invention is represented by the compounds of formula IIB, and salts and prodrugs thereof:

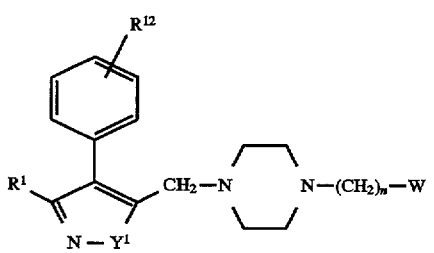

wherein $R^1$ is as defined with reference to formula I above;

$y^1$ represents oxygen or N—$R^5$ in which $R^5$ is as defined with reference to formula I above; and $R^{12}$, n and W are as defined with reference to formula IIA above.

Suitably, $y^1$ is oxygen, NH or N-methyl.

Specific compounds within the scope of the present invention include:

1-benzyl-4-(5-methyl-4-phenyl-1H-pyrazol-3-ylmethyl)-piperazine;
1-benzyl-4-(5-ethyl-4-phenyl-1H-pyrazol-3-ylmethyl)-piperazine;
1-benzyl-4-(4-phenyl-1H-pyrazol-3-ylmethyl)piperazine;
1-(4-chlorobenzyl)-4-(5-methyl-4-phenyl-1H-pyrazol-3-ylmethyl)piperazine;
1-(4-methoxybenzyl)-4-(5-methyl-4-phenyl-1H-pyrazol-3-ylmethyl)piperazine;
1-(2-phenylethyl)-4-(5-methyl-4-phenyl-1H-pyrazol-3-ylmethyl)piperazine;
3-[4-(5-methyl-4-phenyl-1H-pyrazol-3-ylmethyl)piperazinylmethyl]-1H-pyrrolo[2,3-b]pyridine;
1-benzyl-4-(1,3-dimethyl-4-phenyl-1H-pyrazol-5-ylmethyl)-piperazine;
1-benzyl-4-(1-methyl-4-phenyl-1H-pyrazol-3-ylmethyl)-piperazine;
1-benzyl-4-(2-methyl-4-phenyl-2H-pyrazol-3-ylmethyl)-piperazine;
1-benzyl-4-(5(3)-methyl-4-phenylisoxazol-3(5)-ylmethyl)-piperazine;
1-benzyl-4-[4-(4-chlorophenyl)-5-methyl-1H-pyrazol-3-ylmethyl]piperazine;
1-benzyl-4-[5-methyl-4-(2-methylphenyl)-1H-pyrazol-3-ylmethyl]piperazine;
1-(3-chlorobenzyl)-4-(5-methyl-4-phenyl-1H-pyrazol-3-ylmethyl)piperazine;
1-(2-methylbenzyl)-4-(5-methyl-4-phenyl1H-pyrazol-3-ylmethyl)piperazine;
1-(2-chlorobenzyl)-4-(5-methyl-4-phenyl-1H-pyrazol-3-ylmethyl)piperazine;
1-(pyridin-4-ylmethyl)-4-(5-methyl-4-phenyl-1H-pyrazol-3-ylmethyl)piperazine;
1-(pyridin-3-ylmethyl)-4-(5-methyl-4-phenyl-1H-pyrazol-3-ylmethyl)piperazine;
1-(pyridin-2-ylmethyl)-4-(5-methyl-4-phenyl-1H-pyrazol-3-ylmethyl)piperazine;
1-benzyl-4-[4-(2-methylphenyl)-1H-pyrazol-3-ylmethyl]-piperazine;
1-(2-chlorobenzyl)-4-(5(3)-methyl-4-phenylisoxazol-3(5)-ylmethyl)piperazine;
1-(2-methylbenzyl)-4-(5(3)-methyl-4-phenylisoxazol-3(5)-ylmethyl)piperazine;
1-(pyridin-3-ylmethyl)-4-(5(3)-methyl-4-phenylisoxazol-(5)-ylmethyl)piperazine;
1-(4-methylbenzyl)-4-[5-methyl-4-(2-methylphenyl)-1H-pyrazol-3-ylmethyl]piperazine;
1-(4-methylbenzyl)-4-[5(3)-methyl-4-(2-methylphenyl)isoxazol-3(5)-ylmethyl]piperazine;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

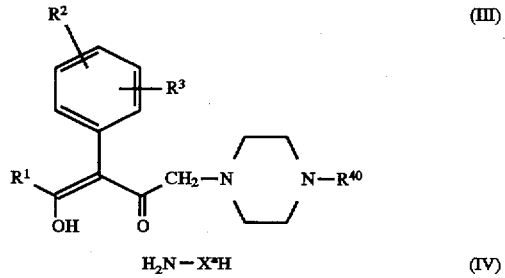

wherein $R^1$, $R^2$ and $R^3$ are as defined above, $R^{40}$ corresponds to the group $R^4$ as defined above or represents an amino-protecting group, and $X^a$ represents oxygen or N—$R^5$ in which $R^5$ is as defined above; followed, where necessary, by removal of the amino-protecting group $R^{40}$ and subsequent attachment of the substituent $R^4$.

Where $X^a$ represents N—$R^5$, the reaction is conveniently carried out by stirring the reactants in a suitable solvent, for example a $C_{1-4}$ alcohol such as methanol. Where $X^a$ represents oxygen, the reaction is typically effected by stirring the reactants in N,N-dimethylformamide, suitably in the presence of a non-nucleophilic base such as ethyldiisopropylamine. Depending upon the nature of the reactants and of the chosen reaction conditions, the reaction may afford the desired product in a single step, or may proceed via a hydroxy intermediate which requires dehydration to convert it into the corresponding product of formula I. The dehydration step may be effected by converting the hydroxy moiety into a leaving group, suitably by treatment with methanesulphonyl chloride and triethylamine in an appropriate solvent such as dichloromethane.

Where the substituent $R^{40}$ represents an amino-protecting group, this group is suitably an alkoxycarbonyl moiety such as t-butoxycarbonyl (BOC), which can conveniently be removed as necessary by treatment under acidic conditions, e.g. stirring in trifluoroacetic acid.

The subsequent attachment of the $R^4$ substituent may suitably be accomplished by conventional means including N-alkylation, where $R^4$ represents, for example, an alkyl or aryl-alkyl group. Typical N-alkylation conditions comprise treating the deprotected amine with an alkyl or aryl-alkyl halide, such as methyl iodide or phenethyl bromide, suitably under basic conditions, e.g. ethyldiisopropylamine in N,N-dimethylformamide. Alternatively, where $R^4$ represents an indol-3-ylmethyl moiety or an aza-analogue thereof, e.g. 7-azaindol-3-ylmethyl, the N-alkylation reaction can conveniently be effected by heating the deprotected piperazine precursor with a gramine or 7-azagramine derivative in toluene at reflux.

As will be appreciated, the overall reaction between compounds III and IV will often give rise to a mixture of isomeric products of formula I, in one of which X represents nitrogen and Y represents oxygen or N—$R^5$, and in the other of which the X and Y moieties are reversed. For this reason, it will generally be necessary at an appropriate stage to separate the mixture of isomers obtained therefrom by conventional methods such as column chromatography.

The intermediates of formula III above may be prepared by reacting a carboxylic acid of formula $R^1$—$CO_2$, or an activated derivative thereof, with a metal enolate of formula V:

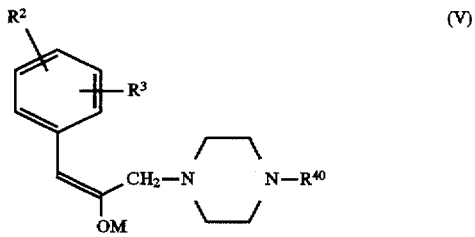

(V)

wherein $R^2$, $R^3$ and $R^{40}$ are as defined above, and M represents a metal capable of providing a suitable counterion for the enolate anion.

The metal M is suitably an alkali metal, especially lithium.

The activated derivative of the carboxylic acid $R^1$—$CO_2H$ is suitably the compound formed by reaction between the carboxylic acid $R^1$—$CO_2H$ and 1,1-carbonyldiimidazole, typically in tetrahydrofuran at room temperature.

The reaction between the carboxylic acid $R^1$—$CO_2H$, or the activated derivative thereof, and compound V is suitably carried out in a solvent such as tetrahydrofuran, typically commencing at −78° C. with warming to room temperature.

The metal enolate of formula V is suitably prepared by reacting the corresponding ketone of formula VI:

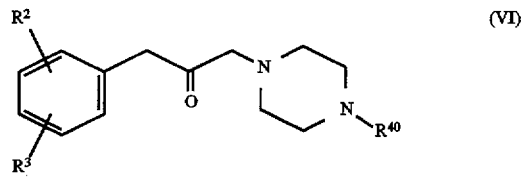

(VI)

wherein $R^2$, $R^3$ and $R^{40}$ are as defined above; with a strong base such as lithium hexamethyldisilazide, typically in tetrahydrofuran at −78° C.

The intermediates of formula VI may be prepared by reacting a compound of formula VII with a compound of formula VIII:

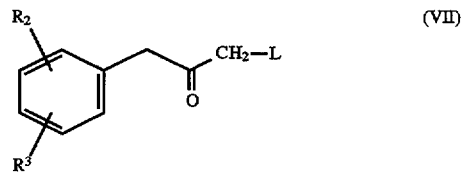

(VII)

(VIII)

wherein $R^2$, $R^3$ and $R^{40}$ are as defined above, and L represents a suitable leaving group.

The leaving group L is suitably a halogen atom, e.g. chlorine, in which case the reaction is conveniently carried out by stirring the reactants under basic conditions in a suitable solvent, e.g. triethylamine in dichloromethane.

Where they are not commercially available, the starting materials of formula VII and VIII may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic*

*Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 µg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 µM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 µM.

EXAMPLE 1

1-Benzyl-4-(5-methyl-4-phenyl-1H-pyrazol-3ylmethyl)-piperazine bis hydrogen oxalate Step A: 1-(4-Benzylpiperazin-1-yl)-3-phenyl-propan-2-one To a solution of 1-chloro-3-phenyl-propan-2-one (10 g, 59 mmol) in dichloromethane (100 ml) was added benzylpiperazine (12.3 ml, 71 mmol) and triethylamine (8.2 ml, 59 mmol). The yellow solution was stirred overnight at ambient temperature and water was added (50 ml). The organic phase was decanted, washed with brine (50 ml), dried (sodium sulphate) and evaporated. The residue was purified by column chromatography on silica using petroleum ether (60–80) ethyl acetate to afford a yellow oil (2.4 g, 13%). $^1$H NMR (250 MHz, $CDCl_3$) δ 2.30–2.64 (8H, m), 3.19 (2H, s), 3.51 (2H, s), 3.74 (2H, s), 7.17–7.38 (10H, m).

Step B: 1-4-Benzylpiperazin-1-yl)-3-phenyl-pentan-2,4-dione

Acetic acid (0.75 ml, 13 mmol) was added to a stirred solution of N,N'-carbonyldiimidazole (2.1 g, 13 mmol) in anhydrous tetrahydrofuran (50 ml). After 30 minutes at ambient temperature a solution of 1-(4-benzylpiperazin-1-yl)-3-phenyl-propan-2-one (2 g, 6.5 mmol) in anhydrous tetrahydrofuran (50 ml) was added. The solution was cooled to −78° C. and lithium bis(trimethylsilyl)amide (1M in tetrahydrofuran, 13 ml) was added dropwise. The resulting mixture was stirred for 45 minutes at −78° C., overnight at room temperature and quenched with a saturated aqueous ammonium chloride solution. The organic layer was separated, dried (sodium sulphate) and evaporated. The residue was purified by column chromatography on silica using petroleum ether (60–80) ethyl acetate, to afford the required product as an oil (530 mg, 23%). $^1$H NMR (250 MHz, $CDCl_3$) δ 1.86 (3H, s), 2.37–2.52 (8H, m), 3.01 (2H, s), 3.58 (2H, s), 7.08–7.45(10H, m).

Step C: 1-Benzyl-1-(5-methyl-4-phenyl-1H-pyrazol-3-ylmethyl)-piperazine bis hydrogen oxalate To a solution of the foregoing diketone (330 mg, 0.94 mmol) in methanol (15 ml) was added hydrazine hydrate (0.55 ml, 9.4 mmol). The solution was stirred at room temperature for 1 hour and evaporated. Dichloromethane (20 ml) and 10% sodium hydroxide solution in water (20 ml) were added to the residue. The organic layer was separated and the aqueous extracted with dichloromethane (20 ml). The combined organics were dried (sodium sulphate) and evaporated to give the title compound free base as a gum (310 mg, 95%). The his hydrogen oxalate salt had mp 226°–230° C. $^1$H NMR (360 MHz, DMSO) δ 2.23 (3H, s), 2.62–2.80 (8H, m), 3.70–3.92 (4H, s), 7.26–7.47 (10H, m). MS, $cI^+$ m/z=347 for $(M+H)^+$. Found: C, 58,80; H, 5.45; N, 10.33. $C_{22}H_{26}N_4 \cdot 2(CO_2H)_2 \cdot 0.25H_2O$ requires C, 58.80; H, 5.79; N, 10.55%.

EXAMPLE 2

1-Benzyl-4-(5-ethyl-4-phenyl-1H-pyrazol-3-ylmethyl)-piperazine bis hydrogen oxalate Carrying out Steps 1a–c whilst replacing acetic acid in Step 1b with propionic acid afforded the titled compound as a solid. mp 224°–227° C. $^1$H NMR (360 MHz, DMSO) δ 1.12 (3H, t, J=7.5 Hz), 2.61 (2H, q, J=7.5 Hz), 2.70–2.96 (8H, m), 3.76 (2H, s), 3.87 (2H, s), 7.26–7.48 (10H, m). MS, $cI^+$ m/z=360 for $(M+H)^+$. Found: C, 58.80; H, 5.80; N, 9.93. $C_{23}H_{28}N_4 \cdot 2(CO_2H)_2 \cdot 0.5H_2O$ requires C, 59.01; H, 6.05; N, 10.19%.

EXAMPLE 3

1-Benzyl-4-(4-phenyl-1H-pyrazol-3-ylmethyl)-piperazine bis hydrogen oxalate

Carrying out Steps 1a–c whilst replacing acetic acid in Step 1b with formic acid afforded the titled compound as a solid. mp 226°–228° C. $^1$H NMR (360 MHz, DMSO) δ 2.66–3.05 (8H, m), 3.80 (2H, s), 4.02 (2H, s), 7.22–7.62 (10H, m), 7.94 (1H, s). MS, $CI^+$ m/z=333 for $(M+H)^+$. Found: C, 57.34; H, 5.92; N, 10.29. $C_{21}H_{24}N_4 \cdot 2(CO_2H)_2 \cdot H_2O$ requires C, 57.50; H, 5.45; N, 10.41%.

EXAMPLE 4

1-(4-Chlorobenzyl)-4-(5-methyl-4-phenyl-1H-pyrazol-3-ylmethyl)-piperazine bis hydrogen oxalate Step A: 4-(4-Chlorobenzyl)-piperazin-1-carboxylic acid tert-butylester To a solution of 4-chlorobenzyl chloride (1.73 g, 10.7 mmol) in ethanol (30 ml) was added tert-butyl-1-piperazine carboxylate (2 g, 10.7 mmol) and potassium carbonate (3 g, 21.4 mmol). The mixture was heated to reflux overnight and the solvent removed. The residue was partitioned between water (50 ml) and dichloromethane (50 ml). The organic layer was separated, dried (sodium sulphate) and evaporated to give the required ester as an oil (3.1 g, 93%). $^1$H NMR (360 MHz, CDCl3) δ 1.45 (9H, s), 2.33–2.41 (4H, m), 3.38–3.45 (4H, m), 3.46 (2H, s), 7.21–7.31 (4H, m). MS, $CI^+$ m/z=311 for $(M+H)^+$.

Step B: 1-(4-Chlorobenzyl)-piperazine

To a solution of the foregoing protected piperazine (3 g, 9.7 mmol) in dichloromethane (30 ml) was added trifluoroacetic acid (7.7 ml, 97 mmol). The solution was stirred at ambient temperature overnight, evaporated and the residue partitioned between a 10% solution of potassium carbonate in water (50 ml) and ethyl acetate (50 ml). The organic layer was decanted and the aqueous phase was extracted with ethyl acetate (3×50 ml). The combined organics were dried (sodium sulphate) and evaporated to give the title product as a low melting solid (2 g, 98%). $^1$H NMR (250 MHz, CDCl$_3$) δ 2.46–2.62 (4H, m), 2.99–3.12 (4H, m), 3.51 (2H, s), 7.20–7.35 (4H, m).

Step C: 1-(4-Chlorobenzyl)-4-(5-methyl-4-phenyl-1H-pyrazol-3-ylmethyl)-piperazine bis hydrogen oxalate The title compound was prepared following procedures described in Steps 1a–c using 1-(4-chlorobenzyl)-piperazine instead of benzylpiperazine in Step 1a. mp 217°–219° C. $^1$H NMR (360 MHz, DMSO) δ 2.23 (3H, s), 2.60–2.92 (8H, m), 3.74 (2H, s), 3.84 (2H, s), 7.24–7.46 (9H, m). MS, CI$^+$ m/z=381 for (M+H)$^+$. Found: C, 53.62; H, 5.27; N, 9.64. C$_{22}$H$_{25}$N$_4$Cl.2(CO$_2$H)$_2$.H$_2$O.requires C, 53.93; H, 5.40; N, 9.68%.

EXAMPLE 5

1-(4-Methoxybenzyl)-4-(5-methyl-4-phenyl-1H-pyrazol-3-ylmethyl)-piperazine bis hydrogen oxalate Carrying out Steps 4a–c whilst replacing 4-chlorobenzyl chloride in Step 4a with 4-methoxybenzyl chloride afforded the titled compound as a solid. mp 222°–224° C. $^1$H NMR (360 MHz, DMSO) δ 2.23 (3H, s), 2.60–3.04 (8H, m), 3.64 (2H, s), 3.75 (3H, s), 3.97 (2H, s), 6.95–7.47 (9H, m). MS, CI$^+$ m/z=377 for (M+H)$^+$. Found: C, 56.53; H, 5.82; N, 9.86. C$_{23}$H$_{28}$N$_4$O.2(CO$_2$H)$_2$.H$_2$O requires C, 56.44; H, 5.86; N, 9.75%.

EXAMPLE 6

1-(2-Phenylethyl)-4-(5-methyl-4-phenyl-1H-pyrazol-3-ylmethyl)-piperazine hydrogen oxalate Step A: 4-(5-Methyl-4-phenyl-1H-pyrazol-3-ylmethyl)-piperazine-1-carboxylic acid tert-butylester Carrying out Steps 1a–c whilst replacing benzylpiperazine in Step 1a with tert-butyl-1-piperazine carboxylate afforded the required compound. $^1$H NMR (250 MHz, CDCl$_3$) δ 1.45 (9H, s), 2.32 (3H, s), 2.36–2.52 (4H, m), 3.35–3.70 (4H, m), 3.39 (2H, s), 7.25–7.45 (5H, m).

Step B: 1-(2-Phenylethyl)-4-(5-methyl-4-phenyl-1H-pyrazol-3-ylmethyl)-piperazine hydrogen oxalate To the foregoing protected piperazine (400 mg, 1.1 mmol) in dichloromethane (10 ml) was added trifluoroacetic acid (0.9 ml, 11 mmol). The solution was stirred at ambient temperature for 5 hours then the solvent was removed. The residue was dissolved in dichloromethane (10 ml) and N,N-diisopropylethylamine (1 ml, 5.75 mmol) was added followed by 1-phenyl-2-bromoethane (0.58 ml, 3.6 mmol). The solution was stirred at room temperature overnight then quenched with a saturated aqueous sodium hydrogen carbonate solution (20 ml). The organic layer was separated and the aqueous extracted with dichloromethane (2×30 ml). The combined organics were dried (sodium sulphate), evaporated and purified by column chromatography on silica using dichloromethane/methanol gradient to afford the title compound free base (73 mg, 18%). The hydrogen oxalate salt had mp 190°–194° C. $^1$H NMR (360 MHz, DMSO) δ 2.21 (3H, s), 2.55–2.65 (4H, m), 2.8–2.94 (8H, m), 3.59 (2H, s), 7.2–7.4 (10H, m). MS, CI$^+$ m/z=361 for (M+H)$^+$. Found: C, 63.78; H, 6.43; N, 11.55. C$_{23}$H$_{28}$N$_4$.1.4(CO$_2$H)$_2$ requires C, 63.69; H, 6.38; N, 11.52%.

EXAMPLE 7

3-[4-(5-Methyl-4-phenyl-1H-pyrazol-3-ylmethyl)-piperazin-1-ylmethyl]-1H-pyrrolo[2,3-b]pyridine Step A: 3-Dimethylaminomethyl-1H-pyrrolo[2,3-b]pyridine A mixture of 1H-pyrrolo[2,3-b]pyridine (18.07 g, 153 mmol), dimethylamine hydrochloride (13.11 g, 161 mmol) and paraformaldehyde (4.92 g, 164 mmol) in n-butanol (500 ml) was heated at reflux for 35 minutes. The mixture was allowed to cool overnight and the precipitated solid collected by filtration. The filtrate was evaporated and the residue triturated with ethyl acetate to afford a second solid. The solids were combined, suspended in saturated aqueous potassium carbonate solution (500 ml) and extracted with dichloromethane (twice). The combined extracts were washed with saturated potassium carbonate (250 ml) then saturated sodium chloride solution (500 ml), dried (magnesium sulphate) then evaporated to a small volume, with the product crystallising out of solution during evaporation. Diethyl ether was added and the title compound collected as a solid (18.13 g, 67%). $^1$H NMR (360 MHz, DMSO) δ 2.19 (6H, s), 3.61 (2H, s), 7.03 (1H, dd, J$_1$=5, J$_2$=8 Hz), 7.36 (1H, d, J=2 Hz), 8.00 (1H, dd, J$_1$=2, J$_2$=8 Hz), 8.20 (1H, dd, J$_1$=2, J$_2$=5 Hz), 11.47 (1H, broad s).

Step B: 3-[4-(5-Methyl-4-phenyl-1H-pyrazol-3-ylmethyl)-piperazin-1-ylmethyl]-1H-pyrrolo[2,3-b]pyridine 4-(5-Methyl-4-phenyl-1H-pyrazol-3-ylmethyl)-piperazin-1-carboxylic acid tert-butylester (365 mg, 1mmol) and trifluoroacetic acid (1.58 ml, 20 mmol) in dichloromethane (10 ml) were stirred at room temperature overnight. 10% Potassium carbonate aqueous solution (40 ml) was added and the organic layer separated. The aqueous solution was extracted with dichloromethane (7×20 ml) and the combined organics dried (sodium sulphate) and evaporated. The residue and 3-dimethylaminoethyl-1H-pyrrolo[2, 3-b]-pyridine (180 mg, mmol) were dissolved in toluene and heated at reflux for 31 hours. A precipitate formed on standing which was filtered and triturated with ethyl acetate to afford the required compound (245 mg, 56%) mp 154°–156° C. $^1$H NMR (360 MHz, CDCl$_3$) δ 2.30 (3H, s), 2.4–2.6 (8H, m), 3.56 (2H, s), 3.69 (2H, s), 7.05 (1H, dd, J$_1$=2, J$_2$=8 Hz ), 7.17 (1H, s), 7.22–7.41 (6H, m), 8.03 (1H, dd, J$_1$=2, J$_2$=8 Hz ), 8.28–8.32 (1H, m), 9.96 (1H, s). MS, CI$^+$ m/z=387 for (M+H)$^+$. Found: C, 71.07; H, 6.84; N, 19.59. C$_{23}$H$_{26}$N$_6$.0.3C$_7$H$_8$.0.6H$_2$O requires C, 70.94; H, 7.02; N, 19.78%.

EXAMPLE 8

1-Benzyl-4-(1,3-dimethyl-4-phenyl-1H-pyrazol-5-ylmethyl1)-piperazine bis hydrogen oxalate Carrying out Steps 1a–c whilst replacing hydrazine hydrate in Step 1c with methylhydrazine afforded the titled compound free base. The bis hydrogen oxalate salt had mp 196°–198° C. $^1$H NMR (360 MHz, DMSO) δ 2.08 (3H, s), 2.37–2.62 (4H, m), 2.81–2.99 (4H, m), 3.52 (2H, s), 3.80 (3H, s), 4.04 (2H, s), 7.22–7.51 (10H, m). MS, CI$^+$ m/z=361 for (M+H)$^+$. Found: C, 58.84; H, 6.01; N, 10.20. C$_{23}$H$_{28}$N$_4$.2(CO$_2$H)$_2$.0.5H$_2$O requires C, 59.01; H, 6.05; N, 10.19%.

EXAMPLE 9

1-Benzyl-4-(1-methyl-4-phenyl-1H -pyrazol-3-ylmethyl1)-piperazine bis hydrogen oxalate Carrying out Steps 1a–c whilst replacing acetic acid in Step 1b with formic acid and hydrazine hydrate in Step 1c with methyl hydrazine afforded a mixture of titled compound and its regioisomer. The mixture was purified by column chromatography on silica using dichloromethane/methanol gradient to yield the required compound free base. The bis hydrogen oxalate had mp 222°–225° C. $^1$H NMR (360 MHz, DMSO) δ 2.66–3.02 (8H, m), 3.74 (2H, s), 3.85 (3H, s), 3.97 (2H, s), 7.22–7.57 (10H, m), 7.98 (1H, s). MS, CI$^+$ m/z=347 for (M+H)$^+$. Found: C, 56.35; H, 5.75; N, 9.71. $C_{22}H_{26}N_4.2(CO_2H)_2.1.5H_2O$ requires C, 56.41; H, 6.01; N, 10.12%.

EXAMPLE 10

1-Benzyl-4-(2-methyl-4-phenyl-2H-pyrazol-3-ylmethyl)-piperazine bis hydrogen oxalate The title compound was obtained using the procedure described in Example 9. The bis hydrogen oxalate had mp 214°–217° C. $^1$H NMR (360 MHz, DMSO) δ 2.50–3.10 (8H, m), 3.69 (2H, s), 3.88 (3H, s), 4.07 (2H, s), 7.23–7.48 (10H, m), 7.58 (1H, s). MS, CI$^+$ m/z=347 for (M+H)$^+$. Found: C, 55.42; H, 5.51; N, 9.24. $C_{22}H_{26}N_4.2.25(CO_2H)_{2.1.5}H_2O$ requires C, 55.26; H, 5.86; N, 9.73%.

EXAMPLE 11

1-Benzyl-4-(5(3)-methyl-4-phenyl-isoxazol-3(5)-ylmethyl)-piperazine bis hydrogen oxalate A solution of 1-[4-benzylpiperazin-1-yl)-3-phenyl-pentan-2,4-dione (4.55 g, 13 mmol), hydroxylamine hydrochloride (3.64 g, 52 mmol) and N,N-diisopropylethylamine (9.2 ml, 52 mmol) and N,N'-dimethyl formamide (80 ml) was heated at 60° C. for 5 hours, cooled to ambient temperature, diluted with water (50 ml) and extracted with ethyl acetate (2×50 ml). The combined organics were dried (sodium sulphate) and evaporated. To the residue in dichloromethane (100 ml) at 0° C. was added methanesulphonyl chloride (1.5 ml, 19 mmol) and triethylamine (4 ml, 26 mmol). The solution was stirred at room temperature overnight then quenched with water. The organic layer was separated, washed with brine, dried (sodium sulphate) and evaporated. The residue was purified by column chromatography on silica using methanol/dichloromethane gradient and recrystallised from ethyl acetate. The bis hydrogen oxalate salt (201 mg, 4.4%) had mp 206°–207° C. $^1$H NMR (360 MHz, MeOH/D$_2$O) δ 2.26 (3H, s), 2.64–2.94 (4H, m), 3.1–3.28 (4H, m), 3.82 (2H, s), 4.29 (2H, s), 7.35–7.51 (10H, m). MS, CI$^+$ m/z=348 for (M+H)$^+$. Found: C, 59.00; H, 5.37; N, 7.59. $C_{22}H_{25}N_3O.2(CO_2H)_2$ requires C, 59.20; H, 5.54; N, 7.97%.

EXAMPLE 12

1-Benzyl-4-[4-(4-chlorophenyl)-5-methyl-1H-pyrazol-3-ylmethyl]-piperazine bis hydrogen oxalate Step A: 1-Chloro-3-(4-chlorophenyl)-propan-2-one The title compound was prepared following a literature procedure (*Eur. J. Med. Chem. Chimica Therapeutica*, 1979, 14(2), 165) and had mp 61°–63° C. $^1$H NMR (250 MHz, CDCl$_3$) δ 3.82 (2H, s), 4.04 (2H, s), 7.07–7.32 (4H, m).
Step B: 1-Benzyl-4-[4-(4-chlorophenyl)-5-methyl-1H-pyrazol-3-ylmethyl]-piperazine bis hydrogen oxalate The title compound was obtained using the procedure described in Example 1 using 1-chloro-3-(4-chlorophenyl)-propan-2-one for 1-chloro-3-phenyl-propan-2-one in Step 1a. The bis hydrogen oxalate had mp 232°–233° C. $^1$H NMR (360 MHz, DMSO) δ 2.33 (3H, s), 2.65–2.95 (8H, m), 3.68 (2H, s), 3.90 (2H, s), 7.35–7.50 (9H, m). MS, CI$^+$ m/z=381 for (M+H)$^+$. Found: C, 54.97; H, 5.10; N, 9.74. $C_{22}H_{25}N_4Cl.2(CO_2H)_2.0.4H_2O$ requires C, 54.96; H, 5.29; N, 9.56%.

EXAMPLE 13

1-Benzyl-4-[5-methyl-4-(2-methylphenyl)-1H-pyrazol-3-ylmethyl]-piperazine bis hydrogen oxalate Step A: 1-Chloro-3-2-methylphenyl)-propan-2-one The title compound was prepared following a literature procedure (*Eur. J. Med. Chem. Chimica Therapeutica*, 1979, 14(2), 165). $^1$H NMR (250 MHz, CDCl$_3$) δ 2.28 (3H, s), 3.92 (2H, s), 4.13 (2H, s), 7.10–7.34 (4H, m).
Step B: 1-Benzyl-4-[5-methyl-(2-methylphenl)-1H-pyrazol-3-ylmethyl]-piperazine bis hydrogen oxalate The title compound was obtained following the procedure described in Example 1 using 1-chloro-3-(2-methylphenyl)-propan-2-one instead of 1-chloro-3-phenyl-propan-2-one in Step 1a and by heating the reaction under refluxing conditions overnight before quenching the reaction in Step 1b. The bis hydrogen oxalate salt had mp 220°–221° C. $^1$H NMR (360 MHz, DMSO) δ 2.00 (3H, s), 2.04 (3H, s), 2.60–2.9 (8H, m), 3.54–3.80 (2H, m), 3.79 (2H, s), 7.08–7.44 (9H, m). MS, CI$^+$ m/z=361 for (M+H)$^+$. Found: C, 58.85; H, 6.00; N, 10.17. $C_{23}H_{28}N_4.2(CO_2H)_2.0.5H_2O$ requires C, 59.01; H, 6.05; N, 10.19%.

EXAMPLE 14

1-(3-Chlorobenzyl)-4-(5-methyl-4-phenyl-1H-pyrazol-3-ylmethyl)-piperazine bis hydrogen oxalate Step A: 1-(3-Chlorobenzyl)-piperazine The title compound was obtained following the procedure described in Steps 4a–b using 3-chlorobenzyl bromide instead of 4-chlorobenzyl chloride in Step 4a. $^1$H NMR (360 MHz, CDCl$_3$) δ 2.60–2.72 (4H, m), 3.03–3.14 (4H, m), 3.65 (2H, s), 7.16–7.44 (4H, m).
Step. B: 1-[4-(3-Chlorobenzyl)-piperazin-1-yl]-3-phenyl-propan-2-one To a solution of 1-chloro-3-phenyl-propan-2-one (2 g, 11.9 mmol) in dichloromethane (30 ml) was added 1-(3-chlorobenzyl)-piperazine (2.5 g, 11.9 mmol) and triethylamine (0.82 ml, 11.9 mmol). The solution was stirred overnight at ambient temperature and a 15% aqueous solution of potassium carbonate (20 ml) was added. The organic phase was decanted and extracted with 2M hydrochloric acid (50 ml). The acidic layer was separated, basified with potassium carbonate and extracted with dichloromethane (2×50 ml). The combined organics were treated with sodium sulphate, potassium carbonate and silica (Kieselgel). The mixture was filtered then evaporated to dryness to afford the required compound as an oil (800 mg, 19%). $^1$H NMR (360 MHz, CDCl$_3$) δ 2.40–2.58 (8H, m), 3.20 (2H, s), 3.48 (2H, s), 3.73 (2H, s), 7.20–7.36 (9H, m).
Step C: 1-(3-Chlorobenzyl)-4-5-methyl-4-phenyl-1H-pyrazol-3-ylmethyl)-piperazine bis hydrogen oxalate Carrying out Step 1b–c whilst replacing 1-(4-benzylpiperazin-1-yl)-3-phenyl-propan-2-one in Step 1b with 1-[4-(3-chlorobenzyl)-piperazin-1-yl]-3-phenyl-propan-2-one afforded the titled compound as a solid, mp 233°–235° C. $^1$H NMR (360 MHz, DMSO) δ 2.24 (3H, s), 2.60–3.00 (8H, m), 3.71 (2H, s), 3.89 (2H, s), 7.26–7.48

(9H, m). MS, Cl⁺ m/z=381 for (M+H)⁺. Found: C, 54.45; H, 4.87; N, 9.52. $C_{22}H_{25}N_4Cl.2(CO_2H)_2.0.5H_2O$ requires C, 54.79; H, 5.30; N, 9.83%.

EXAMPLE 15

1-(2-Methylbenzyl)-4-(5-methyl-4-phenyl-1H-pyrazol-3-ylmethyl)-piperazine bis hydrogen oxalate Carrying out Steps 14a–c whilst replacing 3-chlorobenzyl bromide in Step 14a with 2-methyl benzyl bromide and stirring the solution two hours at reflux instead of overnight at ambient temperature in Step 14b afforded the titled compound as a solid. mp 225°–228° C. ¹H NMR (360 MHz, DMSO) δ 2.23 (3H, s), 2.31 (3H, s), 2.66–3.00 (8H, m), 3.69 (2H, s), 3.89 (2H, s), 7.13–7.47 (9H, m). MS, Cl⁺ m/z=361 for (M+H)⁺. Found: C, 59.79; H, 6.02; N, 10.32. $C_{23}H_{28}N_4.2(CO_2H)_2$ requires C, 59.99; H, 5.96; N, 10.36%.

EXAMPLE 16

1-(2-Chlorobenzyl)-4-(5-methyl-phenyl-1H-pyrazol-3-ylmethyl)-piperazine bis hydrogen oxalate The titled compound was obtained following procedure described in Example 15 using 2-chlorobenzyl chloride for 2-methylbenzyl bromide. mp 219°–221° C. ¹H NMR (360 MHz, DMSO) δ 2.24 (3H, s), 2.60–2.76 (4H, m), 2.84–3.06 (4H, m), 3.67 (2H, s), 4.02 (2H, s), 7.27–7.52 (9H, m). MS, Cl⁺ m/z=381 for (M+H)⁺. Found: C, 55.15; H, 5.04; N, 9.88. $C_{22}H_{25}N_4Cl.2(CO_2H)_2.0.2H_2O$ requires C, 55.31; H, 5.25; N, 9.92%.

EXAMPLE 17

1-(Pyridin-4-ylmethyl)-4-(5-methyl-4-phenyl-1H-pyrazol-3-ylmethyl)piperazine bis hydrogen oxalate Carrying out Steps 14a–c whilst replacing 3-chlorobenzyl bromide in Step 14a with 4-picolyl chloride hydrochloride afforded the titled compound as a solid. mp 186°–189° C. ¹H NMR (360 MHz, DMSO) δ 2.24 (3H, s), 2.77–2.96 (8H, m), 3.82 (2H, s), 3.95 (2H, s), 7.28–7.48 (7H, m), 7.80–7.88 (1H, m), 8.52–8.60 (1H, m). MS, Cl⁺ m/z=348 for (M+H)⁺. Found: C, 54.70; H, 5.14; N, 12.37. $C_{21}H_{25}N_5.2.2(CO_2H)_2.0.5H_2O$ requires C, 55.01; H, 5.52; N, 12.63%.

EXAMPLE 18

(Pyridin-3-ylmethyl)-4-(5-methyl-4-phenyl-1H-pyrazol-3-ylmethyl)-piperazine bis hydrogen oxalate Carrying out Steps 14a–c whilst replacing 3-chlorobenzyl bromide in Step 14a with 3-picolyl chloride hydrochloride afforded the titled compound as a solid. mp 212°–215° C. ¹H NMR (360 MHz, DMSO) δ 2.24 (3H, s), 2.60–3.02 (8H, m), 3.75 (2H, s), 3.91 (2H, s), 7.28–7.48 (6H, m), 7.72–7.79 (1H, m), 8.50–8.56 (2H, m). MS, Cl⁺ m/z=348 for (M+H)⁺. Found: C, 54.56; H, 5.34; N, 12.37. $C_{21}H_{25}N_5.2.1(CO_2H)_2.H_2O$ requires C, 54.38; H, 5.67; N, 12.63%

EXAMPLE 19

1-(Pyridin-2-ylmethyl)-4-5-methyl-4-phenyl-1H-pyrazol-3-ylmethyl)-piperazine bis hydrogen oxalate Carrying out Steps 14a–c whilst replacing 3-chlorobenzyl bromide in Step 14a with 2-picolyl chloride hydrochloride afforded the titled compound as a solid. mp 209°–211° C. ¹H NMR (360 MHz, DMSO) δ 2.24 (3H, s), 2.56–2.70 (4H, m), 2.84–3.02 (4H, m), 3.61 (2H, s), 3.97 (2H, s), 7.30–7.48 (7H, m), 8.48–8.54 (2H, m). MS, Cl⁺ m/z=348 for (M+H)⁺. Found: C, 55.66; H, 5.75; N, 12.94. $C_{21}H_{25}N_5.2(CO_2H)_2.0.5H_2O$ requires C, 55.96; H, 5.64; N, 13.05%.

EXAMPLE 20

1-Benzyl-4-(2-methylphenyl)-1H-pyrazol-3-ylmethyl)-piperazine bis hydrogen oxalate Carrying out Steps 1a–c whilst replacing 1-chloro-3-phenyl-propan-2-one with 1-chloro-3-(2-methylphenyl)-propan-2-one in Step 1b and acetic acid with formic acid in Step 1c afforded the titled compound. The bis hydrogen oxalate had mp>200° C. ¹H NMR (360 MHz, DMSO) δ 2.17 (3H, s), 2.60–2.94 (8H, m), 3.71 (2H, s), 3.85 (2H, s), 7.18–7.44 (9H, m), 7.73 (1H, s). MS, Cl⁺ m/z=347 for (M+H)⁺. Found: C, 57.79; H, 5.68; N, 10.06. $C_{22}H_{26}N_4.2(CO_2H)_2.0.8H_2O$ requires C, 57.73; H, 5.89; N, 10.36%.

EXAMPLE 21

1-(2-Chlorobenzyl)-4-(5(3)-methyl-4-phenyl-isoxazol-3(5)-methyl)-piperazine bis hydrogen oxalate Step A: 1-(2-Chlorobenzyl)-piperazine The title compound was obtained following the procedures described in Step 4a–b using 2-chlorobenzyl chloride instead of 4-chlorobenzyl chloride in Step 4a. ¹H NMR (360 MHz, CDCl₃) δ 2.44–2.64 (8H, m), 3.19 (2H, s), 3.63 (2H, s), 3.74 (2H, s), 7.12–7.48 (4H, m).

Step B: 1-[4-(2-Chlorobenzyl)-piperazin-1-yl]-3-phenyl-pentan-2,4-dione

The required compound was obtained carrying out Steps 1a–b whilst replacing benzylpiperazine in Step 1a with 1-(2-chlorobenzyl)-piperazine. The dione was used crude in the next step.

Step C: 1-(2-Chlorobenzyl)-4(5(3)-methyl-4-phenyl-isoxazol-3(5)-ylmethyl)-piperazine bis hydrogen oxalate The titled compound was prepared following the procedures described in Example 11 using the foregoing diketone instead of 1-(4-benzylpiperazin-1-yl)-3-phenyl-pentan-2,4-dione. The bis hydrogen oxalate had mp 204°–207° C. ¹H NMR (360 MHz, DMSO) δ 2.23 (3H, s), 2.48–2.60 (4H, m), 2.68–2.80 (4H, m), 3.72 (2H, s), 3.87 (2H, s), 7.34–7.58 (9H, m). MS, Cl⁺ m/z=382 for (M+H)⁺. Found: C, 54.58; H, 5.05; N, 7.22. $C_{22}H_{24}N_3OCl.2(CO_2H)_2.0.5H_2O$ requires C, 54.69; H, 5.12; N, 7.36%.

EXAMPLE 22

1-(2-Methylbenzyl)-4-(5(3)-methyl-4-phenyl-isoxazol-3(5)-ylmethyl)piperazine bis hydrogen oxalate Carrying out Steps 21a–c whilst replacing 2-chlorobenzyl chloride in Step 21a with 2-methylbenzyl bromide afforded the titled compound as a solid. mp 204°–207° C. ¹H NMR (360 MHz, DMSO) δ 2.22 (3H, s), 2.31 (3H, s), 2.50–2.64 (4H, m), 2.78–2.94 (4H, m), 3.70 (2H, s), 3.92 (2H, s), 7.17–7.52 (9H, m). MS, Cl⁺ m/z=362 for (M+H)⁺. Found: C, 57.69; H, 5.49; N, 7.99. $C_{23}H_{27}N_3O_2.1(CO_2H)_2.0.7H_2O$ requires C, 58.01; H, 5.83; N, 7.46%.

EXAMPLE 23

1-(Pyridin-3-ylmethyl)-4-(5(3)-methyl-4-phenyl-isoxazol-3(5)-ylmethyl)-piperazine bis hydrogen oxalate Carrying out Steps 21a–c whilst replacing 2-chlorobenzylchloride in Step 21a with 3-picolyl chloride hydrochloride afforded the title compound mp 197°–200° C. $^1$H NMR (360 MHz, DMSO) δ 2.23 (3H, s), 2.44–2.64 (4H, m), 2.68–2.86 (4H, m), 3.69 (2H, s), 3.91 (2H, s), 7.36–7.56 (6H, m), 7.76–7.84 (1H, m), 8.50–8.59 (2H, m). MS, CI$^+$m/z=349 for (M+H)$^+$. Found: C, 55.52; H, 5.12; N, 10.00. $C_{21}H_{24}N_4O \cdot 2(CO_2H)_2 \cdot 0.5H_2O$ requires C, 55.86; H, 5.44; N, 10.42%.

EXAMPLE 24

1-(4-methylbenzyl)-4-[5-methyl-4-(2-methylphenyl)-1H-pyrazol-3-ylmethyl]-piperazine bis hydrogen oxalate Step A: 1-(4-methylbenzyl)-piperazine The title compound was obtained following the procedure described in steps 4a–b using 4-methylbenzyl chloride instead of 4-chlorobenzyl chloride in Step 4a. $^1$H NMR (360 MHz, CDCl$_3$) δ 2.33 (3H, s), 2.40–2.55 (4H, m), 2.90–3.00 (4H, m), 3.51 (2H, s), 7.12 (2H, d, J=8 Hz), 7.19 (2H, d, J=8 Hz).

Step B: 1-[4-(4-methylbenzyl)-piperazin-1-yl]-3-(2-methylphenyl)-propan-2-one

The title compound was obtained following the procedure described in Step 14b using 1-chloro-3-(2-methylphenyl)-propan-2-one instead of 1-chloro-3-phenyl-propan-2-one. $^1$H NMR (360 MHz, DMSO) δ 2.26(3H, s), 2.33 (3H, s), 2.47–2.60 (8H, m), 3.16 (2H, s), 3.48(2H, s), 3.75(2H, s), 7.04–7.20(8H, m). MS, ES$^+$ m/z=337 for (M+H)$^+$.

Step C: 1-(4-methylbenzyl)-4-[5-methyl-4-(2-methylphenyl)-1H-pyrazol-3-ylmethyl]-piperazine bis hydrogen oxalate Carrying out step 1b–c whilst replacing 1-(4-benzylpiperazin-1-yl)-3-phenyl-propan-2-one in step 1b with 1-[4-(3-methylbenzyl)-piperazin-1-yl]-3-(2-methylphenyl)-propan-2-one afforded the title compound as a solid, mp 216°–218° C. $^1$H NMR (360 MHz, DMSO) δ 2.00 (3H, s), 2.04 (3H, s), 2.22 (3H, s), 2.60–2.86 (8H, m), 3.51 (1H, d, J=13 Hz), 3.67 (1H, d, J=13 Hz), 3.81 (2H, s), 7.05–7.30 (8H, m). MS, ES$^+$ m/z=375 for (M+H)$^+$. Found: C, 59.05; H, 5.77; N, 9.50. $C_{24}H_{30}N_4 \cdot 2.3(CO_2H)_2$ requires C, 59.06; H, 5.99; N, 9.63%.

EXAMPLE 25

1-(4-methylbenzyl)- 4-[5(3)-methyl-4-(2-methylphenyl)-isoxazol-3-(5)-ylmethyl]-piperazine bis hydrogen oxalate Step A: 1-[4-methylbenzyl)-piperazin-1-yl]-3-(2-methylphenyl)pentan-2,4-dione The required compound was obtained carrying out Step 1b whilst replacing 1-(4-benzylpiperazin-1-yl)-3-phenyl-propan-2-one with 1-[4-(4-methylbenzyl)-piperazin-1-yl]-3-(2-methylphenyl)-propan-2-one. The dione was used crude in the next step.

Step B: 1-(4-methylbenzyl)-4-[5(3)-methyl-4-(2-methylphenyl)-isoxazol-3(5)-ylmethyl]-piperazine bis hydrogen oxalate The title compound was prepared following the procedure described in Example 11 using the foregoing diketone instead of 1- (4-benzylpiperazin-1-yl )-3-phenyl -pentan-2, 4-dione. The bis hydrogen oxalate had mp. 197°–198° C. $^1$H NMR (360 MHz, DMSO) δ 2.02 (3H, s), 2.07 (3H, s), 2.31 (3H, s), 2.70–2.95 (8H, m), 3.45 (1H, d, J =13 Hz), 3.62 (1H, d, J=13 HZ), 4.00 (2H, s), 7.08–7.36 (8H, m). MS, ES$^+$ m/z=376 for (M+H)$^+$. Found: C, 60.55; H, 5.91; N, 7.32. $C_{24}H_{29}N_3O \cdot 2(CO_2H)_2$ requires C, 60.53; H, 5.99; N, 7.56%.

We claim:

1. A compound of formula I, or a pharmaceutically acceptable salt thereof:

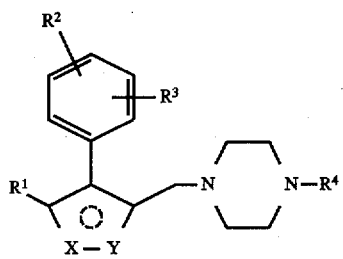

wherein the broken circle represents two non-adjacent double bonds whereby the five-membered ring containing X and Y is aromatic;

one of X and Y represents nitrogen, and other of X and Y represents oxygen or N—R$^5$;

R$^1$ represents hydrogen, C$_{1-6}$alkyl or trifluoromethyl;

R$^2$ and R$^3$ independently represent hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$; wherein hydrocarbon is selected from the group consisting of: C$_{1-6}$alkyl, C$_{2-6}$ alkenyl, C$_{2-6}$ alkynyl, C$_{3-7}$ cycloalkyl, C$_{3-7}$ cycloalkyl(C$_{1-6}$) alkyl, aryl and aryl (C$_{1-6}$)alkyl; and aryl is phenyl or naphthyl; and the heterocyclic group is selected from the group consisting of: C$_{3-7}$heterocycloalkyl, C$_{3-7}$heterocycloalkyl(C$_{1-6}$)alkyl, heteroaryl and heteroaryl(C$_{1-6}$)alkyl; wherein heterocycloalkyl is selected from azetidinyl, pyrrolidyl, piperidyl, piperazinyl and morpholinyl groups; and heteroaryl is selected from: pyridyl, quinolyl, isoquinolyl, pyridazinyl, pyrimidinyl, pyrazinyl, pyranyl, furyl, benzofuryl, dibenzofuryl, thienyl, benzthienyl, indolyl, aza-indolyl, imidazolyl, oxadiazolyl and thiadiazolyl; wherein the hydrocarbon and heterocyclic groups can be substituted by one or more groups selected from C$_{1-6}$alkyl, adamantyl, phenyl, aryl(C$_{1-6}$)alkyl, halogen, C$_{1-6}$ haloalkyl, C$_{1-6}$ aminoalkyl, trifluoromethyl, hydroxy, C$_{1-6}$ alkoxy, aryloxy, keto, C$_{1-3}$ alkylenedioxy, nitro, cyano, carboxy, C$_{2-6}$ alkoxycarbonyl, C$_{2-6}$ alkoxycarbonyl(C$_{1-6}$)alkyl, C$_{2-6}$ alkylcarbonyloxy, arylcarbonyloxy, C$_{2-6}$ alkylcarbonyl, arylcarbonyl, C$_{1-6}$ alkylthio, C$_{1-6}$ alkylsulphinyl, C$_{1-6}$ alkylsulphonyl, arylsulphonyl, trifluoromethane-sulphonyloxy, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —PO(OR$^v$)(OR$^w$), —CONR$^v$R$^w$, —SO$_2$NR$^v$R$^w$ and —CH$_2$SO$_2$NR$^v$R$^w$, in which R$^v$ and R$^w$ independently represent hydrogen, C$_{1-6}$alkyl, aryl or aryl(C$_{1-6}$)alkyl; and R$^4$ represents hydrocarbon or a heterocyclic group, as defined above;

R$^5$ represents hydrogen or C$_{1-6}$alkyl; and

R$^a$ and R$^b$ independently represent hydrogen, hydrocarbon or a heterocyclic group, as defined above.

2. A compound as represented by formula IIA, and salts thereof:

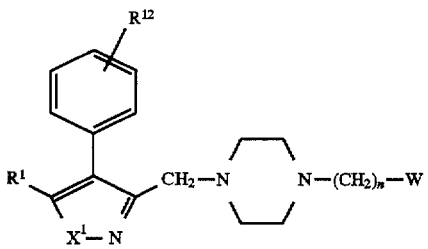
(IIA)

wherein

R¹ is as defined in claim 1;

X¹ represents oxygen or N—R⁵ in which R⁵ is as defined in claim 1;

R¹² represents hydrogen, halogen, cyano, trifluoromethyl, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl;

n is 1, 2, 3 or 4; and w represents a group of formula (i) or (ii):

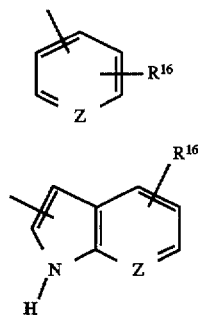

(I)

(II)

in which

Z represents nitrogen or CH; and

R¹⁶ represents hydrogen, halogen, nitro, $C_{1-6}$ alkyl or $C_{1-6}$ alkoxy.

3. A compound as claimed in claim 1 selected from:

1-benzyl-4-(5-methyl-4-phenyl-1H-pyrazol-3-ylmethyl)-piperazine;
1-benzyl-4-(5-ethyl-4-phenyl-¹H-pyrazol-3-ylmethyl)-piperazine;
1-benzyl-4-(4-phenyl-1H-pyrazol-3-ylmethyl)piperazine;
1-(4-chlorobenzyl)-4-(5-methyl-4-phenyl-1H-pyrazol-3-ylmethyl)piperazine;
1-(4-methoxybenzyl)-4-(5-methyl-4-phenyl-1H-pyrazol-3-ylmethyl)piperazine;
1-(2-phenylethyl)-4-(5-methyl-4-phenyl-1H-pyrazol-3-ylmethyl)piperazine;
3-[4-(5-methyl-4-phenyl-1H-pyrazol-3-ylmethyl)piperazin-1-ylmethyl]-1H-pyrrolo[2,3-b]pyridine;
1-benzyl-4-(1,3-dimethyl-4-phenyl-1H-pyrazol-5-ylmethyl)-piperazine;
1-benzyl-4-(1-methyl-4-phenyl-1H-pyrazol-3-ylmethyl)-piperazine;
1-benzyl-4-(2-methyl-4-phenyl-2H-pyrazol-3-ylmethyl)-piperazine;
1-benzyl-4-(5(3)-methyl-4-phenylisoxazol-3(5)-ylmethyl)-piperazine;
1-benzyl-4-[4-(4-chlorophenyl)-5-methyl-1H-pyrazol-3-ylmethyl]piperazine;
1-benzyl-4-[5-methyl-4-(2-methylphenyl)-1H-pyrazol-3-ylmethyl]piperazine;
1-(3-chlorobenzyl)-4-(5-methyl-4-phenyl-1H-pyrazol-3-ylmethyl)piperazine;
1-(2-methylbenzyl)-4-(5-methyl-4-phenyl-1H-pyrazol-3-ylmethyl)piperazine;
1-(2-chlorobenzyl)-4-(5-methyl-4-phenyl-1H-pyrazol-3-ylmethyl)piperazine;
1-(pyridin-4-ylmethyl)-4-(5-methyl-4-phenyl-1H-pyrazol-3-ylmethyl)piperazine;
1-(pyridin-3-ylmethyl)-4-(5-methyl-4-phenyl-1H-pyrazol-3-ylmethyl)piperazine;
1-(pyridin-2-ylmethyl)-4-(5-methyl-4-phenyl-1H-pyrazol-3-ylmethyl)piperazine;
1-benzyl-4-[4-(2-methylphenyl)-1H-pyrazol-3-ylmethyl]-piperazine;
1-(2-chlorobenzyl)-4-(5(3)-methyl-4-phenylisoxazol-3(5)-ylmethyl)piperazine;
1-(2-methylbenzyl)-4-(5(3)-methyl-4-phenylisoxazol-3(5)-ylmethyl)piperazine;
1-(pyridin-3-ylmethyl)-4-(5(3)-methyl-4-phenylisoxazol-3(5)-ylmethyl)piperazine;
1-(4-methylbenzyl)-4-[5-methyl-4-(2-methylphenyl)-1H-pyrazol-3-ylmethyl]piperazine;
1-(4-methylbenzyl)-4-[5(3)-methyl-4-(2-methylphenyl)isoxazol-3(5)-ylmethyl]piperazine; and salts thereof.

4. A process for the preparation of a compound as claimed in claim 1 which comprises reacting a compound of formula III with a compound of formula IV:

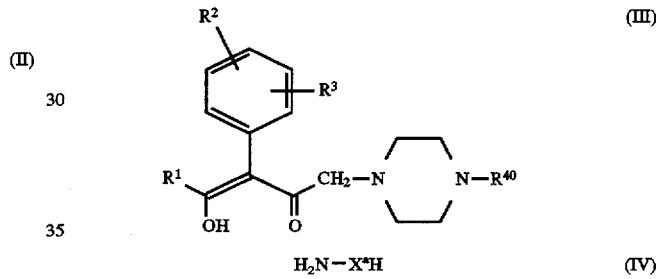

(III)

$H_2N-X^aH$ (IV)

wherein R¹, R² and R³ are as defined in claim 1, R⁴⁰ corresponds to the group R⁴ as defined in claim 1 or represents an amino-protecting group, and $X^a$ represents oxygen or N—R⁵ in which R⁵ is as defined in claim 1; followed, where necessary, by removal of the amino-protecting group R⁴⁰ and subsequent attachment of the substituent R⁴; and subsequently, if desired, converting a compound of formula I initially obtained into a further compound of formula I by conventional methods.

5. A compound as claimed in claim 1 represented by formula IIB, and salts thereof:

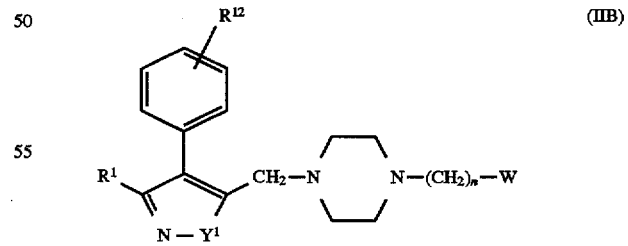

(IIB)

wherein

R¹ is as defined in claim 1;

y¹ represents oxygen or N—R⁵ in which R⁵ is as defined in claim 1;

R¹² represents hydrogen, halogen, cyano, trifluoromethyl, nitro, amino, $C_{1-6}$ alkylamino, di($C_{1-6}$)alkylamino, $C_{1-6}$ alkyl, $C_{1-6}$ alkoxy, aryl ($C_{1-6}$)alkoxy or $C_{2-6}$ alkylcarbonyl;

n is 1, 2, 3 or 4; and

W represents a group of formula (i) or (ii):

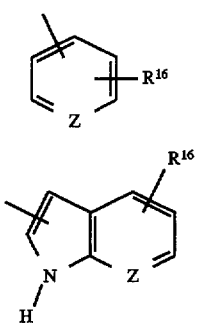

in which

Z represents nitrogen or CH; and
$R^{16}$ represents hydrogen, halogen, nitro, $C^{1-6}$ alkyl or $C^{1-6}$ alkoxy.

6. A compound as claimed in claim 2 wherein $R^{12}$ represents hydrogen, methyl, ethyl, isopropyl, nitro, methoxy or chloro.

7. A compound as claimed in claim 5 wherein $R^{12}$ represents hydrogen, methyl, ethyl, isopropyl, nitro, methoxy or chloro.

8. A compound as claimed in claim 2 wherein $R^{16}$ represents hydrogen, chloro, nitro, methyl or methoxy.

9. A compound as claimed in claim 5 wherein $R^{16}$ represents hydrogen, chloro, nitro, methyl or methoxy.

10. A compound as claimed in claim 6 wherein $R^{16}$ represents hydrogen, chloro, nitro, methyl or methoxy.

11. A pharmaceutical composition comprising an effective amount of a compound of claim 1 and a pharmaceutically acceptable carrier.

12. A pharmaceutical composition comprising an effective amount of a compound of claim 2 and a pharmaceutically acceptable carrier.

13. A pharmaceutical composition comprising an effective amount of a compound of claim 5 and a pharmaceutically acceptable carrier.

14. A pharmaceutical composition comprising an effective amount of a compound of claim 6 and a pharmaceutically acceptable carrier.

15. A pharmaceutical composition comprising an effective amount of a compound of claim 7 and a pharmaceutically acceptable carrier.

16. A pharmaceutical composition comprising an effective amount of a compound of claim 8 and a pharmaceutically acceptable carrier.

17. A pharmaceutical composition comprising an effective amount of a compound of claim 9 and a pharmaceutically acceptable carrier.

18. A pharmaceutical composition comprising an effective amount of a compound of claim 10 and a pharmaceutically acceptable carrier.

19. A method for the treatment of disorders of the dopamine system, which method comprises administering to a patient in need of such treatment an effective amount of a compound as claimed in claim 1.

* * * * *